United States Patent
Mostowfi et al.

(10) Patent No.: US 10,107,728 B2
(45) Date of Patent: Oct. 23, 2018

(54) MICROFLUIDIC SYSTEM AND METHOD FOR PERFORMING A FLASH SEPARATION OF A RESERVOIR FLUID SAMPLE

(75) Inventors: Farshid Mostowfi, Edmonton (CA); Anil Singh, Houston, TX (US); Kurt Schmidt, Oxford (GB); Rob Fisher, Sherwood Park (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1083 days.

(21) Appl. No.: 13/984,852

(22) PCT Filed: Feb. 11, 2011

(86) PCT No.: PCT/IB2011/050573
§ 371 (c)(1),
(2), (4) Date: Jan. 19, 2014

(87) PCT Pub. No.: WO2012/107799
PCT Pub. Date: Aug. 16, 2012

(65) Prior Publication Data
US 2014/0123728 A1   May 8, 2014

(51) Int. Cl.
*G01N 1/40* (2006.01)
*B01D 3/06* (2006.01)
(Continued)

(52) U.S. Cl.
CPC ......... *G01N 1/4022* (2013.01); *B01D 1/0082* (2013.01); *B01D 1/30* (2013.01); *B01D 3/06* (2013.01); *G01N 30/12* (2013.01)

(58) Field of Classification Search
CPC .................................................. E21B 21/067
(Continued)

(56) References Cited

U.S. PATENT DOCUMENTS 2,958,220 A * 11/1960 Kalish ................ G01N 33/2829
73/19.1
3,771,317 A * 11/1973 Nichols .................. B01D 53/18
62/48.2
(Continued)

FOREIGN PATENT DOCUMENTS

EP          2651526 A1    10/2013
GB          2194459        3/1940
(Continued)

OTHER PUBLICATIONS

Examination Report issued in related CA application 2822564 dated Dec. 29, 2014, 4 pages.
(Continued)

*Primary Examiner* — John Fitzgerald

(57) ABSTRACT

A system for performing a flash separation of a reservoir fluid includes a sample chamber configured to hold the reservoir fluid and a flash apparatus in fluid communication with the sample chamber. The flash apparatus includes a microfluidic device configured to flash the reservoir fluid in fluid communication with the sample chamber, and a separation chamber configured to separate the flashed reservoir fluid into a liquid phase and a gaseous phase in fluid communication with the microfluidic device. The system further includes a gas receptacle configured to store the gaseous phase, A method for performing a flash separation of a reservoir fluid includes providing a reservoir fluid to a microfluidic device, urging the reservoir fluid through the microfluidic device such that the reservoir fluid is lashed within the microfluidic device, and separating a liquid phase and a gaseous phase from the flashed reservoir fluid.

25 Claims, 6 Drawing Sheets

(51) Int. Cl.
  *B01D 1/00* (2006.01)
  *B01D 1/30* (2006.01)
  *G01N 30/12* (2006.01)

(58) Field of Classification Search
  USPC .......... 73/23.38, 23.41, 61.41, 61.46, 64.44, 73/64.56; 210/188, 137, 103, 808
  See application file for complete search history.

(56) References Cited

U.S. PATENT DOCUMENTS

| | | | | |
|---|---|---|---|---|
| 4,460,383 | A * | 7/1984 | Valerius | B01D 53/1425 202/181 |
| 5,211,842 | A * | 5/1993 | Tuss | B01D 19/0015 166/75.12 |
| 7,686,959 | B2 * | 3/2010 | Horsman | B01D 15/165 210/143 |
| 8,340,913 | B2 * | 12/2012 | Mostowfi | B01L 3/502784 702/12 |
| 8,380,446 | B2 * | 2/2013 | Mostowfi | B01L 3/5027 702/24 |
| 9,696,193 | B2 * | 7/2017 | Martin | E21B 47/10 |
| 2003/0116195 | A1 * | 6/2003 | Weissgerber | G01N 30/36 137/487.5 |
| 2005/0022940 | A1 * | 2/2005 | Kupper | B01D 1/00 159/47.1 |
| 2006/0008913 | A1 * | 1/2006 | Angelescu | B01D 17/085 436/28 |
| 2007/0054119 | A1 * | 3/2007 | Garstecki | B01J 19/0093 428/402 |
| 2008/0275653 | A1 * | 11/2008 | Cypes | B01D 3/065 702/24 |
| 2009/0211341 | A1 * | 8/2009 | Witt | F04B 51/00 73/49.8 |
| 2011/0030466 | A1 * | 2/2011 | Mostowfi | B01L 3/502784 73/152.12 |
| 2011/0185809 | A1 * | 8/2011 | Guieze | G01N 1/2202 73/32 R |
| 2014/0123728 | A1 | 5/2014 | Mostowfi et al. | |

FOREIGN PATENT DOCUMENTS

| | | | |
|---|---|---|---|
| GB | 1559696 A * | 1/1980 | .......... G01N 1/2035 |
| WO | 2010020435 A1 | 2/2010 | |
| WO | WO2010/020435 * | 2/2010 | |
| WO | 2012107799 A1 | 8/2012 | |

OTHER PUBLICATIONS

Article 94(3) EPC issued in related EP application 11708569.6 dated Dec. 3, 2014, 4 pages.
International Search Report and Written Opinion issued in related PCT application PCT/IB2011/050573 dated Sep. 23, 2011, 94 pages.
Office Action issued in the related EP Application 11708569.6, dated Jul. 13, 2015 (5 pages).
International Preliminary Report on Patentability issued in the related PCT application PCT/IS2011/050573, dated Aug. 13, 2013 (6 pages).
Hoffmann, et al., Equilibrium Constants for a Gas-Condensate System, Transactions of the American Institute of Mining and Metallurgical Engineers, 1953, 198, pp. 1-10.

* cited by examiner

MICROFLUIDIC SYSTEM AND METHOD FOR PERFORMING A FLASH SEPARATION OF A RESERVOIR FLUID SAMPLE

BACKGROUND OF THE INVENTION

Field of the Invention

The present invention relates to a microfluidic system and method for performing a flash separation of a reservoir fluid sample.

Description of Related Art

In the analysis of oilfield reservoir fluids, it is often desirable to determine the gas-oil ratio, the formation volume factor, the monophasic composition, or other such characteristics of a particular reservoir fluid. Typically, the gas-oil ratio is defined as the ratio of the volume of the equilibrium vapor phase to the volume of the equilibrium liquid phase converted to standard conditions. The formation volume factor of the oil is defined as the ratio of the volume of the reservoir fluid at reservoir conditions to the volume of the equilibrium liquid phase of the reservoir fluid at standard conditions. The formation volume factor of the gas is defined as the ratio of the volume of the reservoir fluid at reservoir conditions to the volume of the equilibrium gaseous phase of the reservoir fluid at standard conditions. These characteristics are typically determined using a "flash" system or apparatus. For example, the monophasic composition is determined via a mass balance of the equilibrium vapor and liquid phases resulting from a flash of the reservoir fluid to standard conditions.

Currently, most flash experiments are performed in oilfield fluid analysis laboratories, and sometimes performed directly at the wellsite during wellsite pressure-volume-temperature (PVT) analysis, or are part of specific wellsite tools. Flash apparatus can be divided in two distinct categories: dynamic flash systems and static flash systems. Dynamic flash systems maintain fluid pressure, e.g., reservoir fluid pressure, upstream of a metering valve while maintaining atmospheric conditions downstream of the metering valve. Generally in dynamic flash systems, a pump that drives a single-phase sample and the metering valve are operated manually, which induces variability related to the geometry of the system and the skill level of the operator of the system. Accordingly, conventional dynamic flash experiments are sensitive to the speed at which the experiment is conducted. The accuracy of such experiments generally corresponds to the operator's skill, in that the operator must "feel" the metering valve for the cracking pressure and be very careful not to discharge the oilfield fluid through the metering valve at too high a flow rate. In practice, there is a tendency for the operator to operate the pump and/or the metering valve in such a way that the oilfield fluid flows at too high a rate, resulting in inadequate mass transfer from the liquid phase to the gas phase or vice versa, and erroneous readings. Errors in determining the correct "feel" of the metering valve can lead to liquid carry-over, resulting in inaccuracies in the gas-to-liquid molar ratio or inaccuracies in other such measurements. Moreover, dynamic flash apparatuses typically do not have a gas circulation system and, therefore, the gas does not remain in contact with the liquid for a sufficient amount of time for thermodynamic equilibrium to be attained.

Static flash systems, which are generally used in the laboratory, employ methods wherein a full sample of oilfield fluid is flashed to atmospheric conditions, followed by circulating or bubbling the gaseous phase through the liquid phase until thermodynamic equilibrium is attained. Static flash techniques are generally accepted as being more reproducible, as they do not depend upon the system operator's skill or experiment conditions, such as speed of the experiment. However, static flash methodologies require sophisticated and bulky equipment, which increases cost and requires a large footprint not well suited for field use at the wellsite.

While there are devices for performing a flash separation of reservoir fluid that are well known in the art, considerable shortcomings remain.

BRIEF SUMMARY OF THE INVENTION

In one aspect, the present invention provides a system for performing a flash separation of a reservoir fluid. The system comprises a sample chamber configured to hold the reservoir fluid in fluid communication with a flash apparatus. The flash apparatus comprises a microfluidic device configured to flash the reservoir fluid in fluid communication with the sample chamber and a separation chamber configured to separate the flashed reservoir fluid into a liquid phase and a gaseous phase in fluid communication with the microfluidic device. The system further comprises a gas receptacle configured to store the gaseous phase in fluid communication with the separation chamber.

In another aspect, the present invention provides a system for performing a flash separation of a reservoir fluid. The system comprises a hydraulic pump; a sample chamber comprising a floating piston separating the chamber into a first chamber and a second chamber, the first chamber being in fluid communication with the hydraulic pump; and a flash apparatus. The flash apparatus comprises a microfluidic device configured to flash the reservoir fluid, the microfluidic device defining an entrance passageway and an exit passageway, the entrance passageway being in fluid communication with the second chamber of the sample chamber, and a separation chamber comprising an inlet extending to below an upper reservoir level line and an outlet extending to above the upper reservoir level line, the inlet being in fluid communication with the exit passageway of the microfluidic device. The system further comprises a switching valve in fluid communication with the outlet of the separation chamber, a gas receptacle in fluid communication with the switching valve, and a chromatograph in fluid communication with the switching valve via a fluid line. The system further comprises at least one sensor operably associated with the flash apparatus; at least one temperature control unit operably associated with at least one of the sample chamber, the flash apparatus, and the fluid line; and a controller operably associated with at least one of the hydraulic pump, the switching valve, the chromatograph, the at least one sensor, and the at least one temperature control unit.

In yet another aspect, the present invention provides a method for performing a flash separation of a reservoir fluid. The method includes providing a reservoir fluid to a microfluidic device; urging the reservoir fluid through the microfluidic device such that the reservoir fluid is flashed within the microfluidic device; and separating a liquid phase and a gaseous phase from the flashed reservoir fluid.

The present invention provides significant advantages, including, but not limited to, (1) providing a system and method capable of flashing a reservoir fluid in the field, such at a wellsite or in a portable laboratory, and in a stationary laboratory; (2) providing a system for flashing a reservoir fluid having a smaller footprint than conventional flash systems; (3) providing a system for flashing a reservoir fluid having negligible dead volumes, less calibration, and less liquid entrapment than is typically found in conventional flash systems; (4) providing a system and method for flashing a reservoir fluid that is less dependent upon operator experience, resulting in increased accuracy and repeatability; and (5) providing a system and method for flashing a reservoir fluid that does not require precise throttling of high pressure reservoir fluid flow rates.

Additional objectives, features and advantages will be apparent in the written description which follows.

BRIEF DESCRIPTION OF THE DRAWINGS

The novel features of the invention are set forth in the appended claims. However, the invention itself, as well as a preferred mode of use, and further objectives and advantages thereof, will best be understood by reference to the following detailed description when read in conjunction with the accompanying drawings, in which the leftmost significant digit(s) in the reference numerals denote(s) the first figure in which the respective reference numerals appear, wherein:

Figure 1:
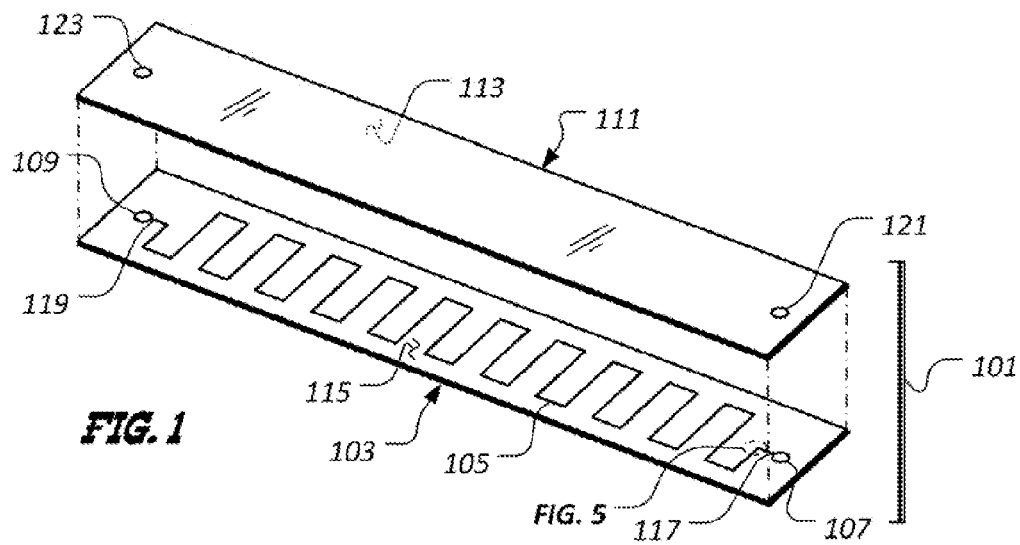
FIG. 1 is a stylized, exploded, perspective view of an illustrative embodiment of a microfluidic device of a system for performing a flash separation of a reservoir fluid sample.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The present invention relates to a microfluidic system and method for performing a flash separation of a reservoir fluid sample. The present system and method employs a microfluidic device defining a serpentine microchannel into which the reservoir fluid is injected. The microfluidic device incorporates features, such as a micro-venturi and one or more constrictions, operably associated with the serpentine microchannel, that induce two-phase flow in the reservoir fluid. Once the two-phase flow is established in the microchannel, rapid equilibrium between gas and liquid is achieved. A two-phase flow can be established in a live liquid oil (containing gas) by inducing bubbles using constrictions in the channel. For a gas condensate, the two-phase flow forms when the pressure of the fluid drops below saturation pressure, in which case liquid hydrocarbon condenses.

A direct flash experiment or test includes changing a reservoir fluid sample from reservoir conditions, where generally a single phase exists, to atmospheric conditions, where liquid and gaseous phases exist. The present invention employs a microfluidic device to induce the change from the single-phase state to the two-phase state. In other words, the single-phase state reservoir fluid is inputted to the microfluidic device and the two-phase state forms within the serpentine microchannel of the microfluidic device as the reservoir fluid travels through the serpentine microchannel. FIG. 1 depicts a stylized, exploded, perspective view of an illustrative embodiment of microfluidic device 101. In the illustrated embodiment, microfluidic device 101 comprises a first substrate 103 defining a serpentine microchannel 105, an entrance well 107 and an exit well 109. In one embodiment, first substrate 103 is about one millimeter thick. Microchannel 105 extends between and is in fluid communication with entrance well 107 and exit well 109. Microchannel 105 forms a serpentine pattern in first substrate 103, thus allowing microchannel 105 to extend a significant length but occupy a relatively small area. In a preferred embodiment, microchannel 105 exhibits a length of one or more meters, a width of between about 15 micrometers and 100 micrometers, and a depth of about 50 micrometers, although the present invention contemplates other dimensions for microchannel 105. The specific dimensions of microchannel 105 are implementation specific, depending upon at least the saturation pressure and viscosity of the reservoir fluid being studied. In one embodiment, microchannel 105 is patterned using a photolithography technique and etched into first substrate 103 by a deep reactive ion etch technique. Microfluidic device 101 further comprises a second substrate 111 having a lower surface 113 that is bonded to an upper surface 115 of first substrate 103. When second substrate 111 is bonded to first substrate 103, such as by anodic bonding, microchannel 105 is sealed except for an inlet 117 at entrance well 107 and an outlet 119 at exit well 109. Second substrate 111 defines an entrance passageway 121 and an exit passageway 123 therethrough, which are in fluid communication with entrance well 107 and exit well 109, respectively, of first substrate 103.

In FIG. 1, first substrate 103 and second substrate 111 are made from glass, such as borosilicate glass, although the present invention contemplates other materials, such as silicon, sapphire, and the like for first substrate 103 and second substrate 111. Exemplary borosilicate glasses are manufactured by Schott North America, Inc. of Elmsford, N.Y., USA, and by Corning Incorporated of Corning, N.Y., USA. Moreover, the present invention contemplates a glass capillary or a metallic capillary, such as a steel capillary, as microchannel 105.

Figure 2:
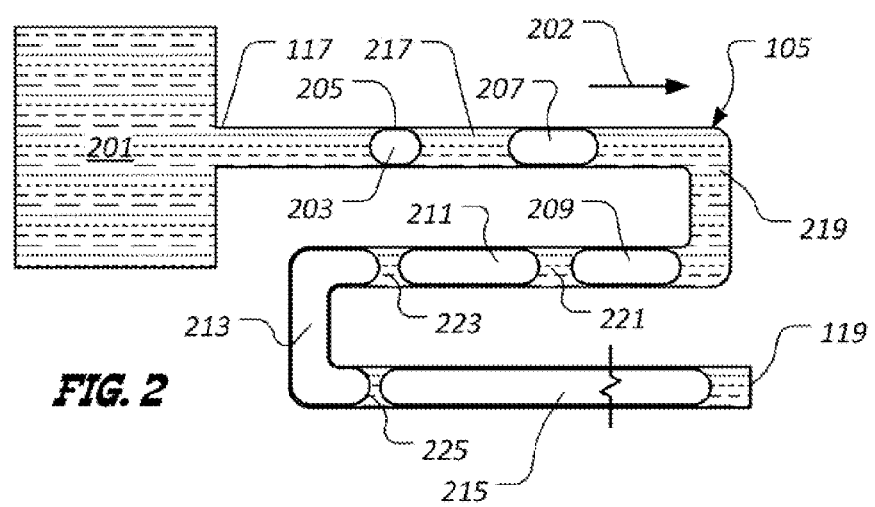
FIG. 2 is a stylized, schematic representation of a reaction of reservoir fluid as the reservoir fluid flows through the microfluidic device of FIG. 1.
Figure 3:
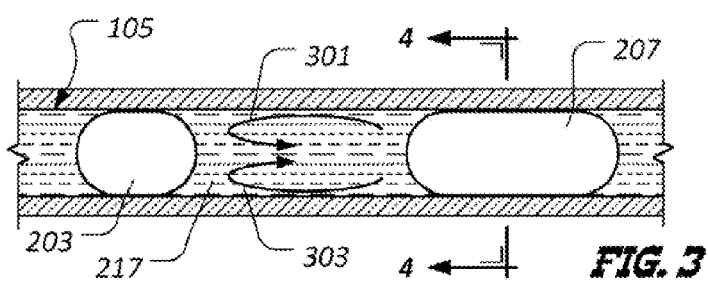
FIG. 3 is an enlarged view of a portion of the representation of FIG. 2 depicting circulations in a slug of reservoir fluid.
Figure 4:
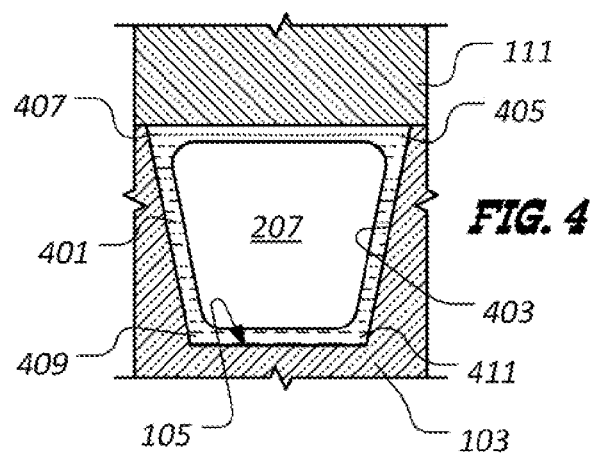
FIG. 4 is a cross-sectional view of the microfluidic device of FIG. 1, as indicated by line 4-4 in FIG. 3, depicting the wetting of a wall of a microchannel of the microfluidic device.

FIG. 2 provides a stylized, schematic representation of the reaction of a reservoir fluid 201 as reservoir fluid 201 flows through microchannel 105 in a direction generally corresponding to arrow 202. When the reservoir fluid enters inlet 117 of microchannel 105, the reservoir fluid is at a pressure above the "saturation pressure" of the reservoir fluid. The saturation pressure of a fluid is the pressure at which a vapor phase (bubbles) begins to evaporate from the mono-phasic fluid phase (Bubble Point; Pb) or the pressure that the liquid phase (droplets) begins to condense from the mono-phasic fluid phase (Dew Point; Pd). When the reservoir fluid exits outlet 119 of microchannel 105, the reservoir fluid is at a pressure below the saturation pressure of the reservoir fluid. Thus, a "first" bubble or "first" drop of liquid 203 forms in the reservoir fluid at some location, e.g., at 205 in FIG. 2, within microchannel 105 where the reservoir fluid is at the saturation pressure. Beyond location 205, multi-phase flow, e.g., gas and liquid flow, of reservoir fluid 201 occurs in microchannel 105. Previously-formed bubbles/liquid droplets, e.g. bubbles 207, 209, 211, 213, 215, and the like, grow in size as reservoir fluid 201 flows within microchannel 105 beyond the location corresponding to the formation of the first bubble/first droplet due to decreased pressure in this portion of microchannel 105 and more evaporation of the lighter components of reservoir fluid 201 or the condensation of heavier components of the fluid. The bubbles are separated by slugs of liquid, such as slugs 217, 219, 221, 223, 225, and the like. Expansion of the bubbles, such as bubbles 207, 209, 211, 213, and 215, results in an increased flow velocity of the bubbles and liquid slugs, such as slugs 217, 219, 221 223, 225, within microchannel 105. In the case of pressures below the dew point (Pd) in the dew point fluid liquid droplets are the slugs separated by gas. The increased amount of the liquid droplets, such as droplets 207, 209 211, 213, and 215, results in a decreased flow velocity of the bubbles and liquid slugs, such as slugs 217, 219, 221, 223, and 225, within microchannel 105. The mass flow rate of reservoir fluid 201 is substantially constant along microchannel 105; however, the volume flow rate of reservoir fluid 201 increases as reservoir fluid flows along microchannel 105. Moreover, as shown in FIG. 3, a plurality of circulations or vortices, represented by arrows 301 and 303, exist in slugs, such as slug 217, of reservoir fluid 201 between bubbles, such as bubbles 203 and 207. Such circulations or vortices enhance mixing in microchannel 105, thus improving the equilibrium between the gas and liquid phases. Furthermore, as shown in FIG. 4, the liquid phase of reservoir fluid, labeled 401 in FIG. 4, wets a wall 403 of microchannel 105. In other words, a thin film of liquid 401 engulfs the bubbles, such as bubble 207, resulting in significant interfacial surface area between the gas and liquid phases. Mass and energy transfer predominantly takes place across such interfacial surfaces, resulting in excellent equilibrium between the phases. It should be noted that the cross-sectional shape of microchannel 105 is non-circular, which enhances thin film formation by enhancing flow in corners 405, 407, 409, and 411 of microchannel 105.

Figure 5:
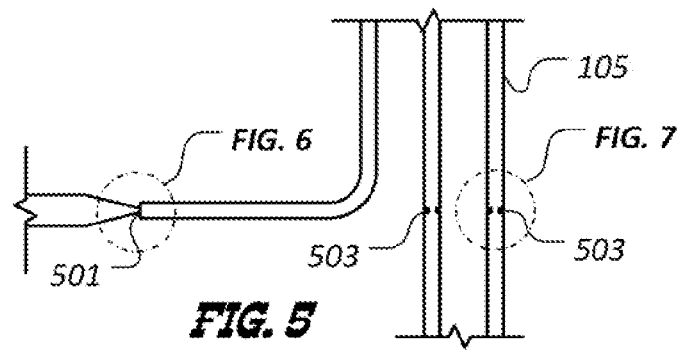
FIGS. 5-7 depict exemplary microchannel constrictions of the microfluidic device of FIG. 1.
Figure 6:
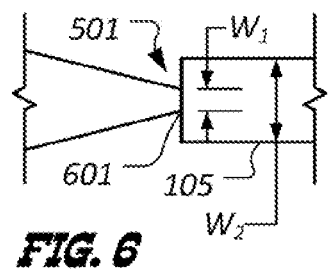
Figure 7:
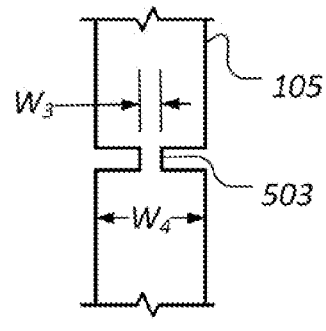

Referring to FIG. 5, one or more portions of microchannel 105 include zones of reduced cross-sectional area to induce the formation of bubble nuclei in the reservoir fluid or droplet nuclei. For example, as shown in FIGS. 5 and 6, a micro-venturi 501 is incorporated into an inlet of microchannel 105. Micro-venturi 501 includes a nozzle opening 601 having a width $W_1$, which is smaller than a width $W_2$ of microchannel 105. The contraction provided by micro-venturi 501 causes a substantial pressure drop in the reservoir fluid at nozzle opening 601 along with an increased velocity of reservoir fluid. The combined effect of the pressure drop and the increased velocity induces formation of bubble nuclei in the reservoir fluid. Preferably, microchannel 105 further includes one or more additional constrictions 503, as shown in FIGS. 5 and 7. Constrictions 503 exhibit widths $W_3$, which are smaller than a width $W_4$ of microchannel 105. Preferably, width $W_1$ of nozzle opening 601 and widths $W_3$ of constrictions 503 are about 20 micrometers, whereas the preferred width $W_2$ and $W_4$ of microchannel 105 is between about 25 and about 100 micrometers. These restrictions increase the velocity of the reservoir fluid up to about 500 percent. It should be noted that the present invention contemplates other devices and/or features for inducing the formation of bubble nuclei in the reservoir fluid, such as small local heating elements.

Figure 8:
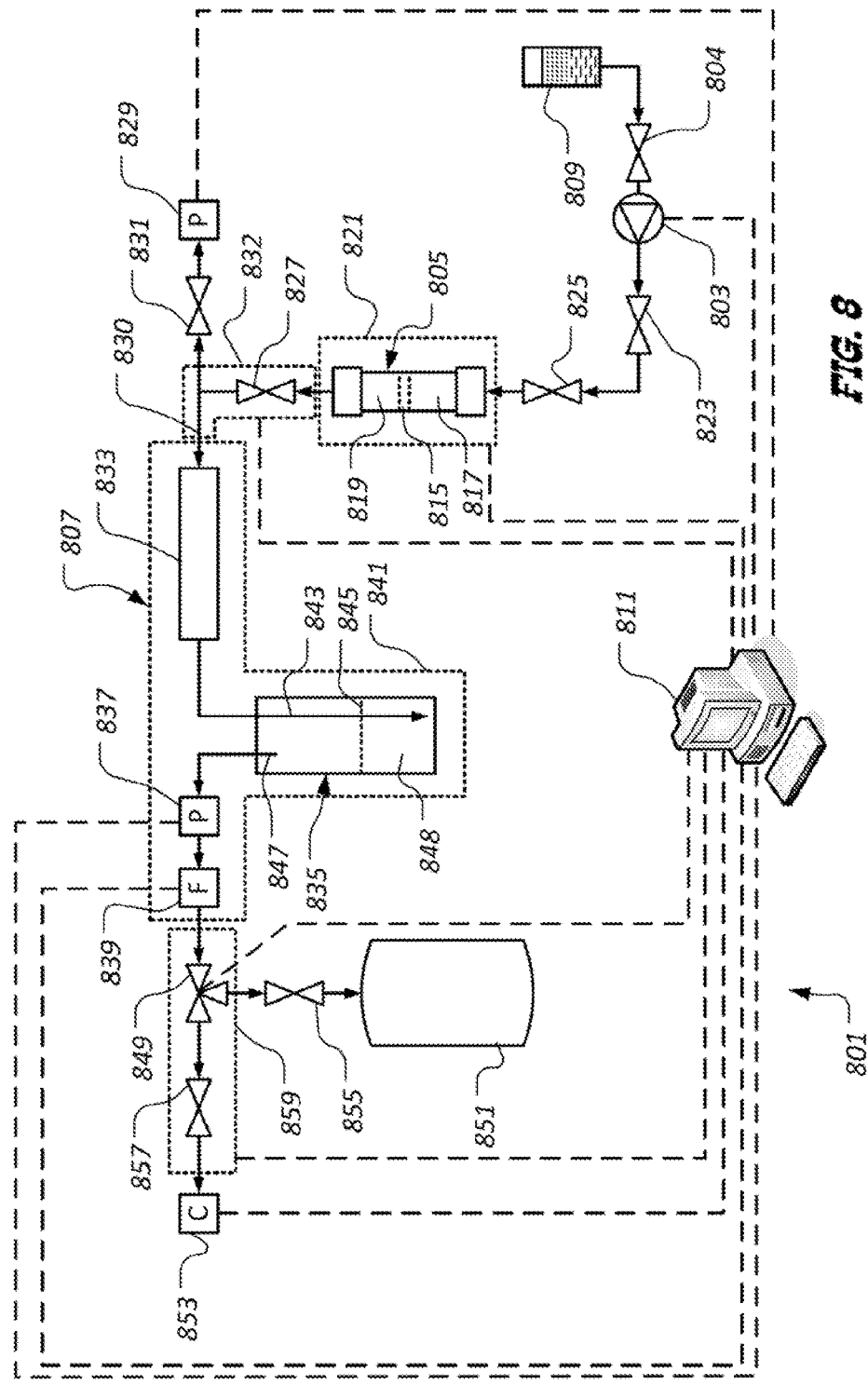
FIG. 8 depicts a stylized, schematic view of a first illustrative embodiment of a microfluidic system of the present invention.

FIG. 8 depicts a schematic view of a first illustrative embodiment of a microfluidic system 801 for performing a flash separation of a reservoir fluid sample. The reservoir fluid sample preferably is conditioned to remove water therefrom and exhibits a single liquid phase prior to processing in system 801; however, the sample may comprise multiple phases, such as a gas trapped in a liquid. System 801 comprises a pump 803 in fluid communication with a sample chamber 805 that, in turn, is in fluid communication with a flash apparatus 807. In general, pump 803 urges a reservoir fluid sample disposed in sample chamber 805 to flash apparatus 807 and maintains desired pressure conditions within sample chamber 805. Flash apparatus 807 is configured to generate atmospheric gas and liquid phases from the reservoir fluid sample at generally atmospheric pressure and at any desired, suitable temperature.

Pump 803 may be any type of pump capable of displacing fluid, such as hydraulic fluid, to exert pressures needed to operate sample chamber 805 and flash apparatus 807. In the illustrated embodiment, pump 803 is a positive displacement pump capable of delivering a defined volume of fluid, such as hydraulic fluid from hydraulic reservoir 809, at a steady, low flow rate and at a defined pressure, preferably without surging. A block valve 804 may be positioned between hydraulic reservoir 809 and pump 803 to shut off hydraulic reservoir 809 if necessary. One example of such a pump 803 is a twin-head, high-pressure, liquid chromatography pump. While the operation of pump 803 may be manually effected, pump 803 is preferably operated by a controller 811 based upon at least parameters inputted to controller 811 and inputs from one or more sensors, transducers, or the like, as discussed in greater detail herein.

Still referring to FIG. 8, sample chamber 805 of the illustrated embodiment comprises a floating piston 815 disposed therein separating chamber 805 into a first chamber 817 and a second chamber 819. Reservoir fluid that is to be characterized is disposed in second chamber 819 and, thus, second chamber 819 is in fluid communication with flash apparatus 807. First chamber 817 is in fluid communication with pump 803, which selectively urges hydraulic fluid from hydraulic reservoir 809 into first chamber 817 of sample chamber 805 to provide a motive force, via floating piston 815, to the reservoir fluid disposed in second chamber 819. The scope of the present invention, however, contemplates configurations of sample chamber 805 other than that illustrated in FIG. 8. Sample chamber 805 is constructed of one or more materials that are suitable for housing the reservoir fluid at testing conditions, such as stainless steel, titanium, or the like. In a preferred embodiment, a temperature control device 821 is operably associated with sample chamber 805. Temperature control device 821, comprising a heating mantle, jacket, elements, or the like, is capable of maintaining sample chamber 805, and thus the reservoir sample disposed therein, at one or more predetermined temperatures, such as at reservoir temperatures, for example at about 850° C. One or more valves 823 and 825 are disposed between pump 803 and sample chamber 805 for interrupting fluid flow between pump 803 and sample chamber 805. An adjustment valve 827 is in fluid communication with second chamber 819 of sample chamber 805 and is utilized to control the flow of reservoir fluid from sample chamber 805. A pressure gage or sensor 829 is in fluid communication with adjustment valve 827 for sensing pressure downstream of adjustment valve 827. In one embodiment, a valve 831 is disposed between and is in fluid communication with adjustment valve 827 and pressure gage or sensor 829 to selectively isolate pressure gage or sensor 829 from the reservoir fluid disposed in second chamber 819 of sample chamber 805.

Flash apparatus 807 is in fluid communication with second chamber 819 of sample chamber 805 via adjustment valve 827 via a line 830, such as flexible metal or plastic tubing. System 801 further includes a heater 832 operatively associated with line 830 for maintaining a temperature of the reservoir fluid as the fluid moves from sample chamber 805 to flash apparatus 807, thus inhibiting substantial variations in temperature that can cause fluctuations in flow rates. In the illustrated embodiment, flash apparatus 807 comprises a microfluidic device 833, a separation chamber 835, a pressure gage or sensor 837, a flow gage or sensor 839, and a temperature control device 841. Entrance passageway 121 (shown in FIG. 1) of microfluidic device 833 is in fluid communication with second chamber 819 of sample chamber 805 via adjustment valve 827. Exit passageway 123 (shown in FIG. 1) of microfluidic device 833 is in fluid communication with an inlet 843 of separation chamber 835, which extends into a liquid phase of reservoir fluid disposed in separation chamber 835. An upper level of the liquid phase of reservoir fluid is represented by a dashed line 845. An outlet 847 extends from separation chamber 835 from a location above the liquid phase of reservoir fluid. Separation chamber 835, in one embodiment, includes a liquid trap portion 848 for temporarily and safely storing the segregated liquid phase of the flashed sample of reservoir fluid. Separation chamber 835 is preferably made of a material chemically inert to natural petroleum analytes, such as hydrocarbons, hydrogen sulfide, carbon dioxide, and the like. Separation chamber 835 may incorporate pressure transducer 837 or other such fluid property sensors in particular embodiments. Outlet 847 of separation chamber 835 is in fluid communication with pressure gage or sensor 837 and flow gage or sensor 839. Temperature control device 841 provides heating and cooling to other components of flash apparatus 807 so that desired temperatures are maintained. For example, in one embodiment, temperature control device 841 is capable of maintaining a temperature of other components of flash apparatus within a range of about 0° C. to about 60° C., although the present invention is not so limited. The particular, desired temperature is implementation-specific, depending at least upon the characteristics and type of reservoir fluid being tested, e.g., heavy oil, lean gas condensates, etc. In one embodiment, the temperature maintained by temperature control device 841 is the standard temperature (15.6° C.), which avoids the necessity of further conversion of the fluid properties from measurement conditions to standard conditions. In conventional methods the apparatus is kept at room temperature, which is usually higher than standard temperature. This results in insufficient condensation, thereby producing inaccurate gas-oil ratio readings. Components of flash apparatus 807 that are exposed to reservoir fluids are preferably constructed from materials generally chemically inert to natural petroleum fluid components, such as hydrocarbons, hydrogen sulfide, carbon dioxide, and the like.

Still referring to FIG. 8, system 801 further comprises a switching valve 849 in fluid communication with flash apparatus 807, a gas storage tag 851, and chromatograph 853, such as a gas chromatograph. System 801 may include valves 855 and 857 for isolating gas storage bag 851 and chromatograph 853, respectively. While not required, a temperature control device 859 provides heating and cooling to the gaseous phase of the reservoir fluid between flash apparatus 807 and chromatograph 853 in the illustrated embodiment so that desired temperatures are maintained. Preferably, the pressure and temperature characteristics of the various components of system 801 are controlled by a controller 811. Accordingly, various components of system 801, such as pump 803, temperature control device 821, and temperature control devices 841 and 859 are controlled based at least upon sensor feedback from pressure gage or sensor 829, pressure gage or sensor 837, flow gage or sensor 839, chromatograph 853, various temperature sensors or gages, and the like.

An exemplary operation of system 801 is now described with reference to FIG. 8. A sample of reservoir fluid is disposed in sample chamber 805, as discussed herein. Adjustment valve 827 is opened to initiate flow of the reservoir fluid through microfluidic device 833, wherein the reservoir fluid achieves a state of equilibrium between liquid and gaseous phases, i.e., the reservoir fluid is "flashed." The two-phase reservoir fluid is routed through inlet 843 of separation chamber 835, such that the liquid phase of the reservoir fluid is trapped therein and the gaseous phase of the reservoir fluid bubbles through the liquid phase of the reservoir fluid. The gaseous phase of the reservoir fluid then flows through outlet 847, interacting with pressure gage or sensor 837 and gas flow gage or sensor 839. Once the flow of the gaseous phase of the reservoir fluid is detected at gas flow gage or sensor 839, pump 803 is controlled, for example, by human means or by controller 811, to maintain a flow of the gaseous and liquid fractions at a desired rate. Controller 811 may receive feedback from pressure gage or sensor 837, which is representative of the pressure in separation chamber 835 to control downstream pressure to maintain or adjust the pressure to atmospheric pressure or another desired pressure. Separation chamber 835, in combination with microfluidic device 833, function to separate and temporarily store the gas and liquid phases of the flashed sample of reservoir fluid at atmospheric conditions as the flashed sample exits the outlet of microfluidic device 833, i.e., exit passageway 123 of microfluidic device 101, shown in FIG. 1. The gaseous phase leaving separation chamber 835 is measured by gas flow gage or sensor 839, which is configured to measure any gas leaving separation chamber 835, by way of volume or mass, at any given flash condition, that is, at atmospheric pressure or another pressure and at a predetermined downstream temperature. Gas flow gage or sensor 839 may be of any suitable type, for example, a positive displacement type, a cumulative flow rate type, a mini-coriolis type, a thermal type, a transport type, or the like, capable of accurately measuring low rates of gas flow. When a thermal type flow gage or sensor is employed, another device, such as a mini-calorimeter, may be placed downstream of the flow gage or sensor so that an accurate estimation of the heat capacity can be determined to derive an accurate correction factor for the flow gage or sensor.

The gaseous phase then flows from gas flow gage or sensor 839 to switching valve 849, which is configured to provide direct injection of the gas into chromatograph 853 or a gas receptacle, such as a gas storage bag 851. While not required, temperature control device 859 maintains the gaseous phase entering chromatograph 853 at a temperature slightly higher than the temperature maintained in flash apparatus 807 to avoid heavy component condensation, which could bias the molecular composition to be measured by chromatograph 853. The composition of the gaseous phase can be analyzed a plurality of times by chromatograph 853 using fast gas chromatography, for example, for both verifying the constant process and for calculating physical properties, such as density, specific heat, and the like, of the gaseous phase that, in some implementations, are needed for gas flow to volume conversions.

As noted herein, the gaseous phase of the flashed reservoir fluid may also be collected in gas storage bag 851, which preferably has a larger volume capacity than the maximum expected volume of gas produced by system 801. Access to gas storage bag 851 is provided by switching valve 849 and, if present, valve 855. Gas storage bag 851 is constructed of materials generally inert to the natural components of hydrocarbons. Gas storage bag 851 collects the evolved gaseous phase exiting flash apparatus 807 and not routed to chromatograph 853. Moreover, gas storage bag 851, in combination with switching valve 849, can be used to maintain a desired pressure, such as atmospheric pressure, in the downstream gaseous phase volume by varying the flow of the gaseous phase into gas storage bag 851. It should be noted that the present invention contemplates other devices and methods for maintaining the desired pressure in the downstream gaseous phase volume, such as a pump, a piston-cylinder, or the like, which may be controlled by controller 811. Preferably, gas storage bag 851 does not add a significant differential pressure to the gaseous phase as gas is collected in bag 851. The gaseous phase collected in gas storage bag 851 may be further analyzed or disposed of in an environmentally-safe manner.

Volumes of the liquid phase of the flashed reservoir fluid may be determined from, for example, mass and density measurements of the liquid disposed in separation chamber 835. Utilizing mass and density measurements to determine volume is preferred, as more accurate determinations for small quantities of the liquid phase can be accomplished in this manner.

System 801 may be used, for example, in website fluid analysis, such as pressure-volume-temperature analysis, sample validation, or the like; flow metering applications, such as multiphase flow measurements; separator applications, and the like.

Figure 9:
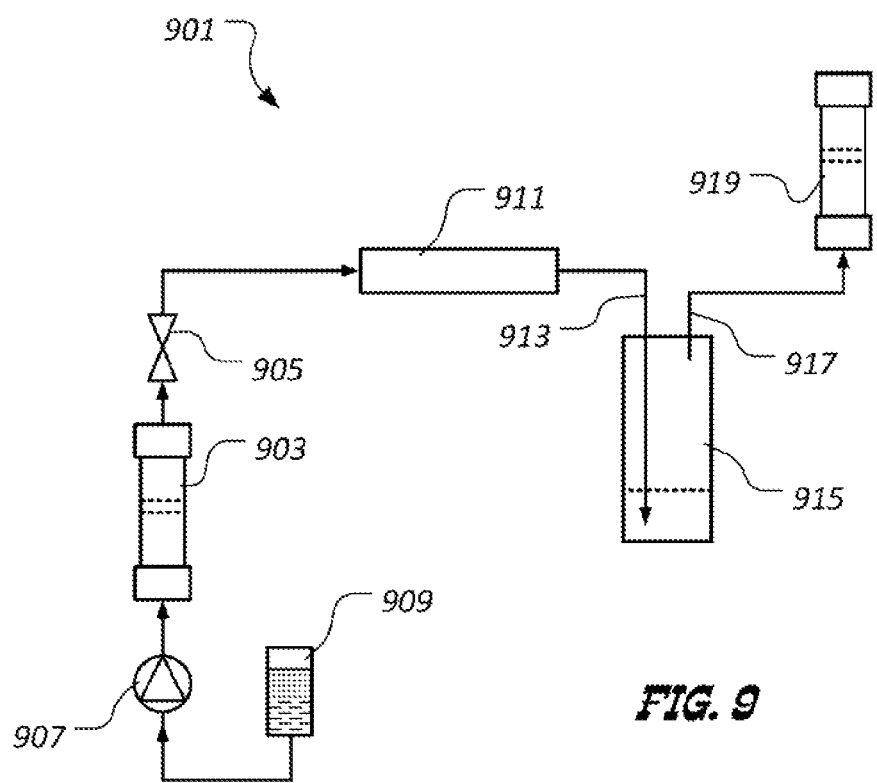
FIG. 9 depicts a stylized, schematic view of a second illustrative embodiment of a microfluidic system of the present invention.

FIG. 9 depicts a second illustrative embodiment of a microfluidic system 901 for performing a flash separation of a reservoir fluid sample. In the illustrated embodiment, system 901 comprises a sample chamber 903 in fluid communication with a valve 905 corresponding to adjustment valve 827 of FIG. 8. In one embodiment, sample chamber 903 is a pressurized chamber in which the reservoir sample is disposed. Alternatively, sample chamber 903 corresponds to sample chamber 805 of FIG. 8 and system 901 comprises a pump 907 that urges a fluid, such as hydraulic fluid, from reservoir 909 to sample chamber 903 to pressurize the reservoir fluid sample disposed therein. Adjustment valve 905 is in fluid communication with an input of a microfluidic device 911, such as microfluidic device 101 of FIG. 1. An output of microfluidic device 911 is in fluid communication with an input 913 of a separation chamber 915, corresponding in one embodiment to separation chamber 835 of FIG. 8. An output 917 of separation chamber 915 is in fluid communication with a gas receptacle 919, which may be a piston-cylinder as shown in FIG. 9; a gas storage bag, such as gas storage bag 851 of FIG. 8, or the like. As discussed herein, the reservoir fluid sample disposed in sample chamber 903 is flashed in microfluidic device 911. The liquid phase of the reservoir fluid sample is retained in separation chamber 915, while the gaseous phase is retained in gas receptacle 919. Both the liquid phase and the gaseous phase are retained for analysis.

Figure 10:
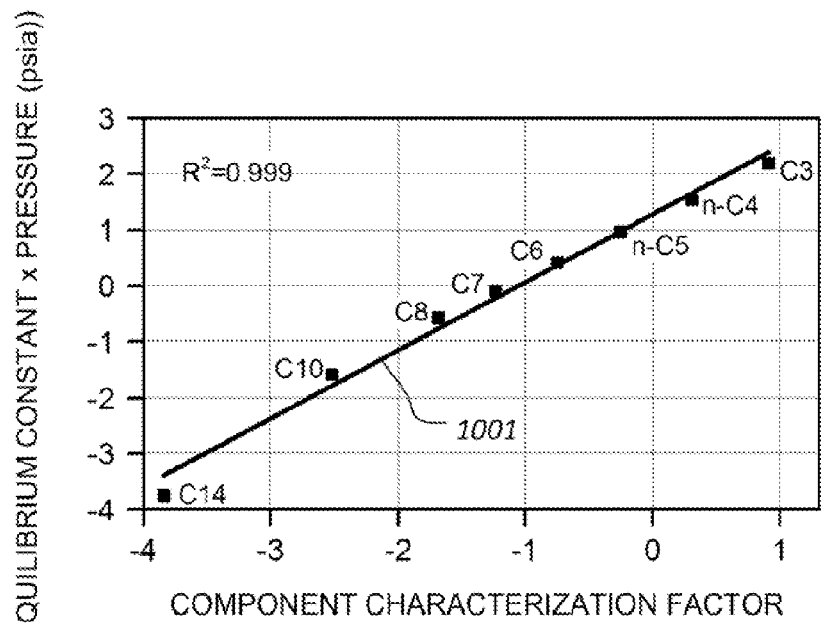
FIGS. 10-12 depict graphical representations of data obtained from experiments comparing the method of the present invention, a direct flash technique, and a static flash with vapor circulation technique.
Figure 12:
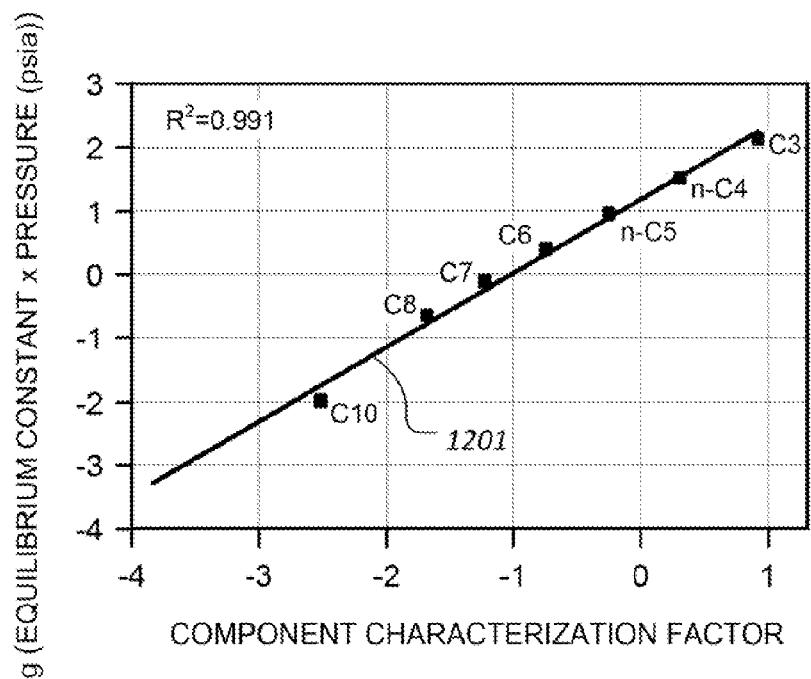
Figure 11:
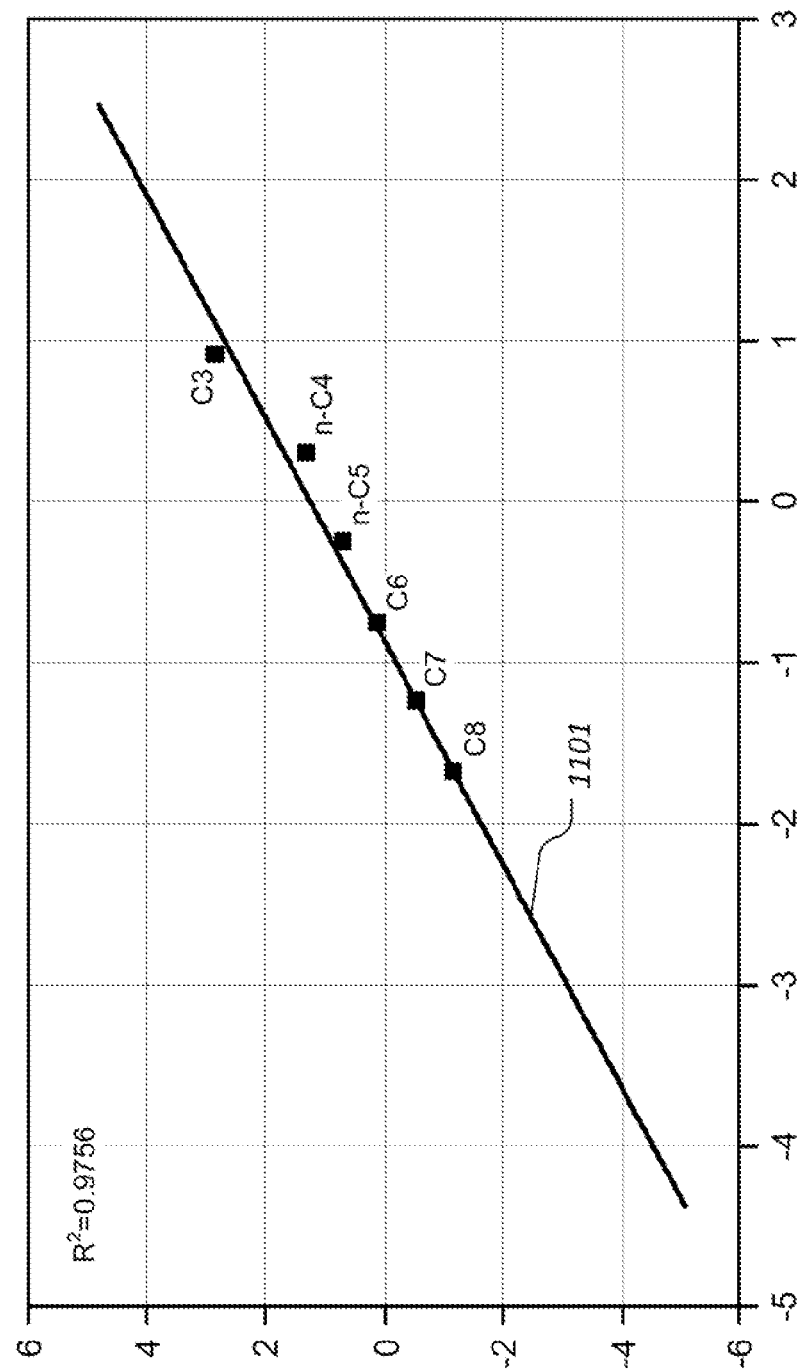

The embodiment of system 901 was utilized in an experiment compare the present system and method of performing a flash separation of a reservoir fluid sample to a conventional direct flash methodology and a conventional static flash with vapor circulation methodology. FIGS. 10, 11, and 12 depict Hoffmann plots, i.e., log(equilibrium constant× pressure(psia)) versus component characterization factor, for each of the method of the present invention, direct flash method, and static flash with vapor circulation method, respectively. Regarding FIG. 10, use of the method of the present invention resulted in a highly linear plot 1001, indicating good internal consistency of the equilibrium ratios of the measured reservoir fluid sample. Moreover, FIG. 10 shows that the measured data exhibits a coefficient of determination ($R^2$) of 0.999, which indicates that the data fits linear plot 1001 very well. Regarding FIG. 11, which represents data obtained using a conventional direct flash methodology, the data exhibits an $R^2$ value of 0.9756, which is lower than the $R^2$ value for the method of the present invention, indicating that the direct flash data fails to fit linear plot 1101 as well as the data obtained using the method of the present invention fits linear plot 1001. Moreover, no C10 was detected in the vapor phase using the direct flash method, possibly indicating that equilibrium was not achieved between the liquid and gaseous phases. As shown in FIG. 12, which represents data obtained using a conventional static flash with vapor circulation methodology, the data exhibits an $R^2$ value of 0.991, indicating the data fits linear plot 1201 better than the fit exhibited using the direct flash technique (FIG. 11) but not as well as the fit exhibited using the method of the present invention (FIG. 10).

The experiment yielded gas-oil ratios (scf/bbl) of 658±3.6 using the method of the present invention, 626 using the conventional direct flash technique, and 650 using the static flash with vapor circulation technique. The method of the present invention yielded the highest gas-oil ratio, which corresponds to the Hoffmann plot of FIG. 10, wherein heavier components in the gaseous phase were liberated in microfluidic device 911. The experiment yielded gas molecular weights of 25.60 using the method of the present invention, 23.33 using the conventional direct flash technique, and 25.27 using the static flash with vapor circulation technique. The data indicate that use of the direct flash technique results in about a 10 percent error in molecular weight, due to the lack of heavier components in the gaseous phase as a result of poor equilibrium.

It should be noted that the present system may employ microfluidic devices having configurations other than those described herein and shown in the drawings.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below. Although the present invention is shown in a limited number of forms, it is not limited to just these forms, but is amenable to various changes and modifications.

What is claimed is:

1. A system for performing a flash separation of a reservoir fluid, comprising:
    a sample chamber configured to hold the reservoir fluid;
    a flash apparatus, comprising:
        a microfluidic device configured to flash the reservoir fluid in fluid communication with the sample chamber by means of an adjustment valve and comprising a serpentine microchannel having a micro-venturi, including a nozzle opening having a width smaller than that of the microchannel, in an inlet thereof, wherein flashing of the reservoir fluid is initiated by one or more constrictions therein; and
        a separation chamber configured to separate the flashed reservoir fluid into a liquid phase and a gaseous phase, the separation chamber in fluid communication with the microfluidic device and comprising an inlet in fluid communication with the microfluidic device extending into a liquid phase of reservoir fluid in a liquid trap portion in the separation chamber and an outlet extending from above the liquid phase of reservoir fluid in the separation chamber; and
    a gas receptacle configured to store the gaseous phase in fluid communication with the separation chamber outlet.

2. The system of claim 1, wherein the separation chamber comprises:
    an inlet in fluid communication with the microfluidic device extending below an upper reservoir fluid line; and
    an outlet in fluid communication with the gas receptacle extending to above the upper reservoir fluid line.

3. The system of claim 1, further comprising:
    a switching valve in fluid communication with the gas receptacle and the separation chamber; and
    a chromatograph in fluid communication with the switching valve.

4. The system of claim 1, wherein the gas receptacle is a gas storage bag.

5. A method for performing a flash separation of a reservoir fluid, comprising:
    providing a reservoir fluid to a microfluidic device according to the system of claim 1;
    urging the reservoir fluid through the microfluidic device, such that the reservoir fluid is flashed within the microfluidic device; and
    separating a liquid phase and a gaseous phase from the flashed reservoir fluid.

6. The method of claim 5, wherein urging the reservoir fluid through the microfluidic device is accomplished by operating a pump.

7. The method of claim 5, further comprising collecting the gaseous phase in a gas receptacle.

8. The method of claim 5, further comprising analyzing the gaseous phase using chromatography.

9. The system of claim 1, wherein the microfluidic device comprises:
    a first substrate defining a microchannel, an entrance well, and an exit well, the microchannel extending between and in fluid communication with the entrance well and the exit well; and
    a second substrate attached to the first substrate to form a microfluidic device, the second substrate defining an entrance passageway in fluid communication with the entrance well and an exit passageway in fluid communication with the exit well;
    wherein the entrance passageway is in fluid communication with the sample chamber and the exit passageway is in fluid communication with the separation chamber.

10. The system of claim 9, wherein a lower surface of the second substrate is fused to an upper surface of the first substrate using an anodic bonding method.

11. The system of claim 9, wherein at least one of the first substrate and the second substrate comprises one of glass and silicon.

12. The system of claim 9, wherein the microchannel, the entrance well, and the exit well are generated in the first substrate by an etching process.

13. The system of claim 9, wherein the microchannel exhibits a serpentine shape and a length of at least one meter.

14. The system of claim 9, wherein the microchannel exhibits a width within a range of tens of micrometers to hundreds of micrometers.

15. The system of claim 9, wherein the microchannel includes a microventuri inlet having a nozzle opening that exhibits a smaller width than a width of the microchannel.

16. The system of claim 9, wherein the microchannel includes at least one constriction exhibiting a width that is smaller than a width of the microchannel.

17. The system of claim 1, further comprising a pump for urging the reservoir fluid from the sample chamber.

18. The system of claim 17, wherein:
    the sample chamber comprises a floating piston dividing the sample chamber into a first chamber and a second chamber;
    the reservoir fluid is disposed in the second chamber; and
    the pump is in fluid communication with the first chamber, such that the pump is configured to urge a fluid into the first chamber to urge the reservoir fluid from the second chamber.

19. The system of claim 17, further comprising at least one gage or sensor operably associated with the flash apparatus.

20. The system of claim 19, further comprising a controller operably associated with the pump and the at least one gage or sensor.

21. The system of claim 20, further comprising a switching valve in fluid communication with the flash apparatus and the gas receptacle and operably associated with the controller.

22. The system of claim 20, further comprising a chromatograph in fluid communication with the flash apparatus and operably associated with the controller.

23. The system of claim 20, further comprising at least one temperature control device operably associated with at least one of the sample chamber, the flash apparatus, and a fluid line extending from the flash apparatus.

24. The system of claim 23, wherein the at least one temperature control device is operably associated with the controller.

25. A system for performing a flash separation of a reservoir fluid, comprising:
    a hydraulic pump;

a sample chamber comprising a floating piston separating the chamber into a first chamber and a second chamber, the first chamber being in fluid communication with the hydraulic pump;

a flash apparatus, comprising:
   a microfluidic device configured to flash the reservoir fluid, the microfluidic device defining an entrance passageway and an exit passageway, the entrance passageway being in fluid communication with the second chamber of the sample chamber by means of an adjustment valve and comprising a serpentine microchannel having a micro-venturi, including a nozzle opening having a width smaller than that of the microchannel, in an inlet thereof, wherein flashing of the reservoir fluid is initiated by one or more constrictions therein; and
   a separation chamber comprising an inlet extending to below an upper reservoir level line and an outlet extending to above the upper reservoir level line, the inlet being in fluid communication with the exit passageway of the microfluidic device in a liquid trap portion in the separation chamber, and an outlet extending from above the upper reservoir level line of reservoir fluid in the separation chamber;

a switching valve in fluid communication with the outlet of the separation chamber;

a gas receptacle in fluid communication with the switching valve;

a chromatograph in fluid communication with the switching valve via a fluid line;

at least one sensor operably associated with the flash apparatus;

at least one temperature control unit operably associated with at least one of the sample chamber, the flash apparatus, and the fluid line; and a controller operably associated with at least one of the hydraulic pump, the switching valve, the chromatograph, the at least one sensor, and the at least one temperature control unit.

* * * * *